(12) United States Patent
Jervis

(10) Patent No.: US 7,396,362 B2
(45) Date of Patent: Jul. 8, 2008

(54) PROSTHESIS AND METHOD FOR DEPLOYMENT WITHIN A BODY LUMEN

(75) Inventor: James E. Jervis, Atherton, CA (US)

(73) Assignee: General Surgical Innovations, Inc., North Haven, CT (US)

( * ) Notice: Subject to any disclaimer, the term of this patent is extended or adjusted under 35 U.S.C. 154(b) by 0 days.

(21) Appl. No.: 10/244,765

(22) Filed: Sep. 16, 2002

(65) Prior Publication Data

US 2003/0023298 A1 Jan. 30, 2003
US 2007/0150040 A9 Jun. 28, 2007

Related U.S. Application Data

(63) Continuation of application No. 09/411,517, filed on Oct. 4, 1999, now Pat. No. 6,451,025, which is a continuation of application No. 08/627,667, filed on Apr. 1, 1996, now Pat. No. 6,533,805.

(51) Int. Cl.
*A61F 2/84* (2006.01)

(52) U.S. Cl. ............................................. 623/1.11

(58) Field of Classification Search ........... 623/1.11, 623/1.18, 1.22, 1.49, 23.7, 23.71; 606/108, 606/99, 191, 192, 194, 198; 604/103
See application file for complete search history.

(56) References Cited

U.S. PATENT DOCUMENTS

| | | | |
|---|---|---|---|
| 3,620,212 A | 11/1971 | Fannon et al. | |
| 3,786,806 A | 1/1974 | Johnson et al. | |
| 3,890,977 A | 6/1975 | Wilson | |
| 4,037,324 A | 7/1977 | Andreasen | |
| 4,170,990 A | 10/1979 | Baumgart et al. | |
| 4,233,690 A | 11/1980 | Akins | |
| 4,425,919 A | 1/1984 | Alston, Jr. et al. | |
| 4,503,569 A | 3/1985 | Dotter | |
| 4,505,767 A | 3/1985 | Quin | |
| 4,553,545 A | 11/1985 | Maass et al. | |

(Continued)

FOREIGN PATENT DOCUMENTS

RU 2 108 764 C1 * 4/1998

(Continued)

OTHER PUBLICATIONS

S.M. Andrews & A.W. Anson, "Shaper memory alloys in minimally invasive therapy", Blackwell Science Ltd, Minimally Invasive Therapy 1995: 4:315-318.

(Continued)

*Primary Examiner*—Dave Willse

(57) ABSTRACT

A stent and catheter for implanting or removing a helical-shaped stent within a body passageway; the catheter having an elongate sheath with a socket for securing one end of the stent at a distal region of the sheath and an inner member extending from the sheath, and also having a socket at a distal region of the inner member for securing the other end of the stent. The inner member is rotatable relative to the sheath to transmit torque to the stent to permit unwinding of the helical stent at its limiting strain to expand the stent. Also discussed are methods for performing procedures for implanting or removing a helical stent from a body passageway.

23 Claims, 8 Drawing Sheets

U.S. PATENT DOCUMENTS

| | | | |
|---|---|---|---|
| 4,665,906 A | 5/1987 | Jervis |
| 4,665,918 A | 5/1987 | Garza et al. |
| 4,733,665 A | 3/1988 | Palmaz |
| 4,795,458 A | 1/1989 | Regan |
| 5,007,926 A | 4/1991 | Derbyshire |
| 5,037,427 A | 8/1991 | Harada et al. |
| 5,067,957 A | 11/1991 | Jervis |
| 5,089,005 A | 2/1992 | Harada |
| 5,160,341 A | 11/1992 | Brenneman et al. |
| 5,190,546 A | 3/1993 | Jervis |
| 5,197,978 A | 3/1993 | Hess |
| 5,219,358 A | 6/1993 | Bendel et al. |
| RE34,327 E | 7/1993 | Kreamer |
| 5,242,451 A | 9/1993 | Harada et al. |
| 5,246,445 A | 9/1993 | Yachia et al. |
| 4,733,665 A | 1/1994 | Palmaz |
| 5,282,824 A | 2/1994 | Gianturco |
| 5,372,660 A | 12/1994 | Davidson et al. |
| 5,405,377 A | 4/1995 | Cragg |
| 5,441,516 A | 8/1995 | Wang et al. |
| 5,443,500 A | 8/1995 | Sigwart |
| 5,466,242 A | 11/1995 | Mori |
| 5,474,563 A | 12/1995 | Myler et al. |
| 5,476,505 A | 12/1995 | Limon |
| 5,476,508 A | 12/1995 | Amstrup |
| 5,507,771 A | 4/1996 | Gianturco |
| 5,545,210 A | 8/1996 | Hess et al. |
| 5,556,413 A | 9/1996 | Lam |
| 5,562,697 A | 10/1996 | Christiansen |
| 5,569,296 A | 10/1996 | Marin et al. |
| 5,571,135 A | 11/1996 | Fraser et al. |
| 5,571,168 A | 11/1996 | Toro |
| 5,597,378 A | 1/1997 | Jervis |
| 5,766,239 A | 6/1998 | Cox |

FOREIGN PATENT DOCUMENTS

| | | |
|---|---|---|
| WO | WO 95/32757 | 12/1995 |
| WO | WO 96/26682 | 9/1996 |
| WO | WO 96/31249 | 10/1996 |
| WO | WO 96/37167 | 11/1996 |

OTHER PUBLICATIONS

Endocoil Biliary Endoprosthesis, "New Flexibility in Management of Malignant Biliary Obstructions".

* cited by examiner

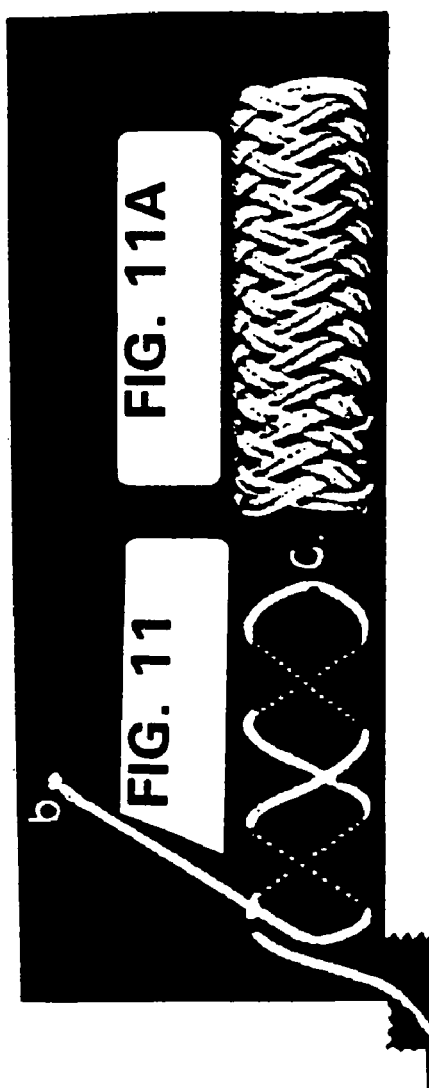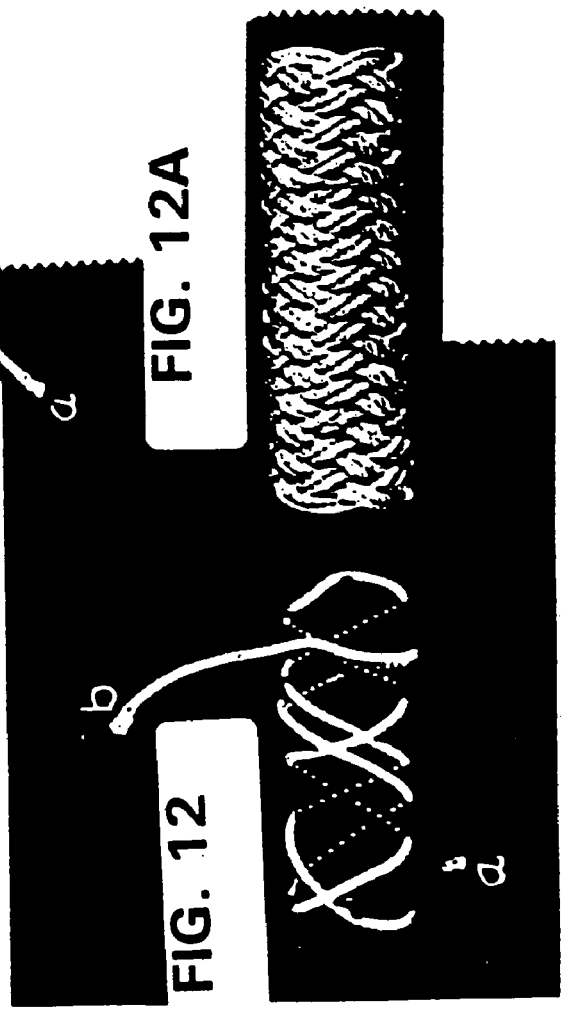

PROSTHESIS AND METHOD FOR DEPLOYMENT WITHIN A BODY LUMEN

CROSS-REFERENCE TO RELATED APPLICATIONS

This application is a continuation of U.S. application Ser. No. 09/411,517, filed Oct. 4, 1999, now U.S. Pat. No. 6,451,025, which is a continuation of U.S. application Ser. No. 08/627,667, filed Apr. 1, 1996, now U.S. Pat. No. 6,533,805.

FIELD OF THE INVENTION

This invention relates to catheters for deployment and/or removal of prostheses in a body passageway, methods of using such catheters for prosthesis deployment and/or removal, and novel prostheses including helical stents for opening a body passageway.

BACKGROUND OF THE INVENTION

The use of shape memory alloys or intermetallics and, specifically, Nitinol in the construction of medical devices is well known (Andrews et al., Minimally Invasive Therapy 4:315-318 (1995), Quin, U.S. Pat. No. 4,505,767; these and all other references cited herein are expressly incorporated by reference as if fully set forth herein in their entirety). Nitinol has been used as dental arch wire (Andreasen, U.S. Pat. No. 4,037,324), catheters (Wilson, U.S. Pat. No. 3,890,977), heart valves (Akins, U.S. Pat. No. 4,233,690), IUDs (Fannon, U.S. Pat. No. 3,620,212), bone plates (Johnson et al., U.S. Pat. No. 3,786,806), marrow nails (Baumgart, U.S. Pat. No. 4,170,990), stents (Hess, U.S. Pat. No. 5,197,978, and Mori, U.S. Pat. No. 5,466,242), vena cava filters, staples, and clips. The properties of these materials have been extensively discussed in the above-noted references and, for the sake of brevity, will not be repeated here. All of the referenced devices have characteristics which make or tend to make them impractical. Often, they require heating or cooling which is not always convenient or reliable. Loss of temperature control can cause shape change before the device is placed properly or before the surgeon is prepared for the shape change or force generation effect delivered by the device. Sometimes, in addition, when force generation is the desired effect, heat-driven shape change restrained by an element against which the force is directed (e.g., bone) results in total conversion to austenite. Austenite has a reasonably high Young's modulus (on the order of 14 million PSI). Therefore, the residual stress or force which is generated in equilibrium initially cannot be maintained because slight changes in geometry or strain results in significant changes in stress. These slight changes in strain might be brought about by differential thermal expansion, or creep, as a result of tissue growth or accommodation in response to the force generated by the device, or by tissue atrophy.

An improvement was disclosed by Jervis, U.S. Pat. No. 4,665,906, and its progeny. This art discloses the use of pseudoelasticity to effect shape change or force generation at essentially constant temperature, in the case of medical devices, at or around body temperature. Pseudoelastic phenomena in Nitinol is brought about by the fact that stress may be used, within defined temperature and composition limits, to convert austinite to martensite. After an initial range of Hookian behavior, this austenite-to-martensite conversion occurs at essentially constant stress as loading increases. Within still further defined temperature limits, unloading causes reversion to austenite, again at essentially constant (but lower) stress. The loading/unloading sequence therefore defines a relatively flat hysteresis loop. The dimensions of this loop can be altered somewhat by alloying, or by thermal and mechanical treatment; but typical values might include a spread of from 25 to 50 KSI between the loading and unloading plateaus, and up to around 5% or more strain at essentially constant stress. At strains beyond the plateau range, the stress again rises or falls at essentially Young's modulus, as it does initially.

Hysteresis behavior to generate shape change or force at or around constant (body) temperature is discussed in Jervis, U.S. Pat. No. 4,665,906. Shape changes resulting from this phenomenon can be significant compared to strain ranges available with conventional metals (those without austenite/martensite transformations), and forces delivered can be relatively well controlled over a wide strain range. U.S. Pat. No. 4,665,906 discusses forming the device to the final shape desired, straining the device in a direction which tends to facilitate placement into the body, restraining the device in this strained shape during insertion into or placement near the body, then releasing all or part of the device such that it returns or tends to return to the desired shape.

Among the medical devices discussed above, prostheses adapted to hold open a body passageway by expansion, such as stents, have recently been the subject of growing interest. The concept of using an expandable prosthesis to open a body passageway is discussed generally in Palmaz, U.S. Pat. No. 4,733,665, Cragg, U.S. Pat. No. 5,405,377, Gianturco, U.S. Pat. No. 5,282,824, Derbyshire, U.S. Pat. No. 5,007,926, Sigwart, U.S. Pat. No. 5,443,500, and Yachia et al., U.S. Pat. No. 5,246,445. Meanwhile, Hess, U.S. Pat. No. 5,197,978, discusses the use of a martensite nitinol stent which is deployed by inflating a balloon to expand the martensite. Building on the stent art, others have sought to employ shape memory alloys so that an expandable stent member can be implanted with thermal activation. See Kleshinski et al., International Application No. PCT/US95/03931, Regan, U.S. Pat. No. 4,795,458, Harada, U.S. Pat. No. 5,089,005, and Harada et al., U.S. Pat. No. 5,037,427.

The Regan '458 patent teaches use of a helical Nitinol coil which expands from one diameter to another in response to application of heat. This is use of Nitinol in its oldest heat-to-change form. However, it has been observed that such use presents problems in several ways. The temperature excursions to which the body may be subjected without damage is limited. The ability to alloy Nitinol for accurate transition temperatures is difficult. The ability to control the temperature of a Nitinol device being implanted within the body is also difficult, with the danger being the shape change may occur inadvertently and potentially disastrously. The transition temperature itself is, in reality, a range of temperatures over which shape change occurs. Accordingly, there is a need to devise a stent in which use of or reliance upon temperature is eliminated as a relevant parameter in the behavior of the stent.

BRIEF SUMMARY OF THE INVENTION

We have made an unexpected discovery of two ways to overcome the limitations discussed above. The first is to utilize martensitic Nitinol, and the other is to use non-reversible pseudoelastic Nitinol. In either case, work to transform the stent from one shape to another is performed within the body. Whether martensite or non-reversible pseudoelastic material is preferable depends in part on the strength required of the expanded stent. The stress/strain performance of either material provides opportunity for approaches utilizing the material in bending. In bending, the maximum strain at any point is inversely proportional to the radius of curvature at that point. When an element of constant cross-section is bent, it seldom bends uniformly (in the theoretical sense, only in pure bending). Continued loading beyond the plateau of either the martensite or the pseudoelastic material leads to a sharp rise in modulus, which means that, at the end of the plateau, the material at maximum strain is getting stronger than adjacent material which is still operating on the plateau. Gross bending of a device of uniform geometry will therefore eventually result in all elements being bent to the same strain, i.e., a circle.

For the purposes of stent deployment, there is a substantial significance associated with the ability of a material to deform with all elements eventually being bent to the same strain. For example, a small helical stent made from materials that have these properties will permit maximum unwinding which forms, after the unwinding force is removed, an enlarged helix with any cross-section being substantially circular, rather than having a kinked wire in the shape of an oval, ellipse, or other irregular geometric shape. Moreover, the enlarged helix will have a substantially uniform diameter throughout its length, meaning that the surface of the stent defines substantially a regular cylinder, rather than an irregular geometry. The unwinding of a stent to produce an enlarged stent having a substantially uniform cylindrical interior volume is a property with important physiological ramifications because a stent with irregular kinking which protrudes into the vessel lumen may create an obstruction and lead to blood flow constriction. Although described in terms of a helix, other structures which are to be deformed and must approach a predetermined shape can make similar use of this plateau-dependent behavior.

In accordance with the invention, one approach to making, for example, a vascular stent is to form a small coil for introduction purposes. When located properly in the vessel, one end of the coil is "unscrewed" relative to the other, increasing the coil diameter until the stent is against the vessel wall in the desired manner, and essentially at the end of the plateau strain range. The plateau shape of the stress/strain curve means that, assuming the original coil was uniform in diameter and of uniform thickness strip or wire, the final diameter of the stent would also be uniform. Simple mathematical relationships exist which relate the geometry requirements and material capabilities. End features may be added for cooperation with tools or catheters for placement utilizing torsion control. By addition of end features which could be "caught" at a later date, the stent could be "screwed" together, reducing its diameter for removal. Such a stent could be contained within or coated with an outer member, e.g., Dacron™, which could be left in place after the Nitinol is removed. Furthermore, if it is known ahead of time that this sort of stent is to be left in place, it may be unnecessary to utilize a PCTA catheter before placing the stent depending in part on the extent of the stenosis. The expansion of the stent would dilate the vessel as the stent is deployed.

A further advantage of using the stents disclosed herein is that the force of radial expansion is not limited to stored energy as is the case for self-expanding stents made from shape memory alloys. This factor is an important consideration when dealing with calcified, hardened regions of a vessel which are difficult to enlarge. In these regions, a greater force of expansion may be needed to achieve a given diameter lumen. Such greater force can be applied in accordance with the present invention because the application of force is completely controlled during stent deployment. This ability to control force represents yet another improvement of the present invention over self-expanding stents which exert an expansion force which is limited by the energy stored prior to deployment.

BRIEF DESCRIPTION OF DRAWINGS

FIGS. 11, 11A, 12, and 12A depict Turk's Head structures suitable for application to an interwoven stent in accordance with an alternative embodiment of the present invention.

DETAILED DESCRIPTION OF THE INVENTION

Figure 1:
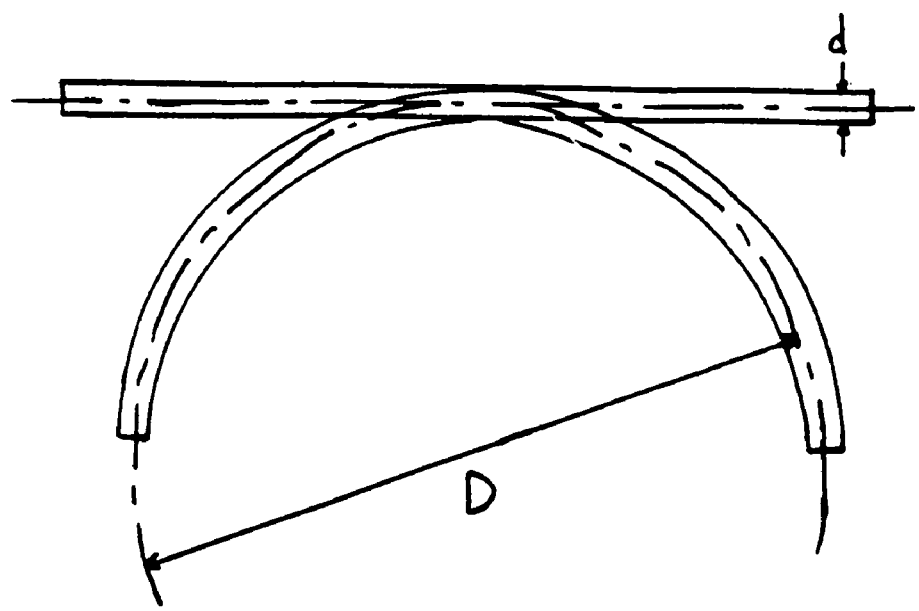
FIG. 1 depicts a bending wire and the parameters which are relevant to a quantitative determination of strain, namely diameter of wire (d) and diameter of curvature (D)

We have developed a stent which can be expanded to a uniform diameter in a vessel without reliance on temperature-dependent properties and without occluding vessel flow during deployment. With reference to FIG. 1, the strain for a bending wire, strip, or sheet is given as $\epsilon = d/D$. See Timoshenko & Young, "Elements of Strength of Materials," Van Nostrand (1962), page 112. When the shape change is from curve to curve, the strain change $\epsilon_L$ is given by subtraction as $\epsilon_L = (d/D_1) - (d/D_2)$.

Figure 2:
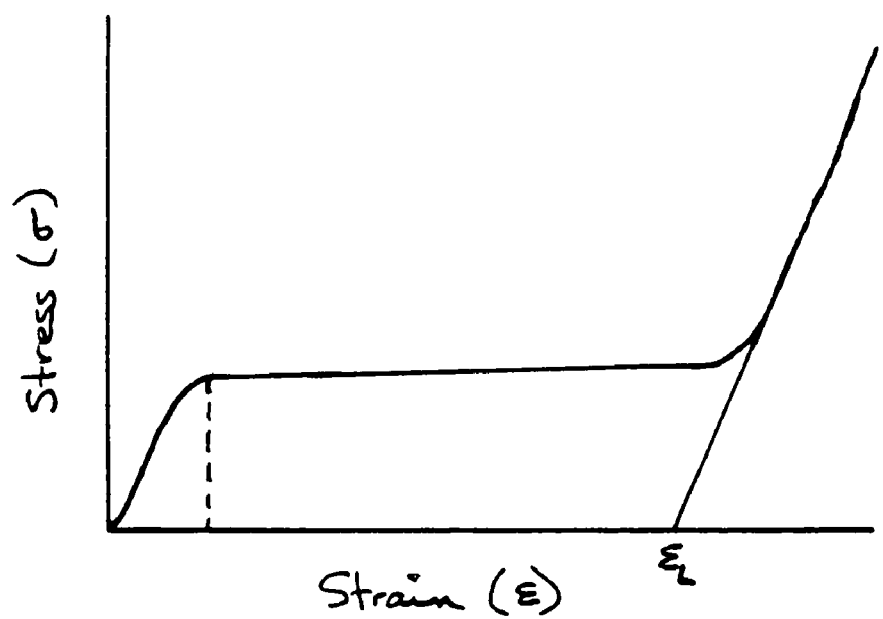
FIG. 2 depicts a stress/strain curve for material having martensite properties or a pseudoelastic material without complete hysteresis.

Preferred materials for stents as disclosed herein include those having a stress/strain curve as shown in FIG. 2. The modulus E for these materials is given by the equation $$E = \frac{\sigma}{\epsilon}$$

Assuming a modulus for austenite of 14 million psi and a stress of 10 ksi, or 10,000 psi, one can solve for strain $$\epsilon = \frac{10 \times 10^3 \, psi}{14 \times 10^6 \, psi} = 0.714 \times 10^{-3}$$

Thus, on these assumptions, referring to FIG. 2, the plateau region begins at a strain of 0.000714 where the stress at the plateau region is 10 ksi. The stress produced in the alloy is essentially constant regardless of the strain provided when the strain lies within the plateau region of the stress/strain curve. This means that a known, relatively constant force (calculable from the height of the stress plateau) can be applied over a wide (up to 5% or more) strain range.

Exemplary materials include those having martensitic properties or pseudoelastic properties without complete hysteresis, e.g., materials specifically disclosed in Quin, U.S. Pat. No. 4,505,767, having FIG._1B properties as described by Quin. Examples include alloys of Ni, Ti, and V having an atomic percent composition, respectively, of 41.5:38.5:20.0, 36.25:33.75:30.0, 47.75:45.75:6.5, 47.5:45.5:7.0, 48.5:46.5:5.0, 45.0:45.0:10.0, 47.5:46.5:6.0, 46.5:46.5:7.0, 48.25:46.25:5.5, and more preferably of 48.0:46.0:6.0, the later composition exhibiting appropriate mechanical behavior for use as a stent herein at temperatures of 0-50° C. It is desirable that the stent alloy display incomplete hysteresis at human body temperature (37° C.), more preferably at broader ranges including 35-40° C., more preferably 30-42° C., more preferably 25-44° C., more preferably 20-46° C., more preferably 15-48° C.

When such materials are "bent" or, in the case of the stent, unwound, an increase in strength at the totally strained end of the plateau will cause all elements to have strain $\epsilon_L$ when bent sufficiently. Therefore, a small coil can be unwound to form a larger coil of uniform diameter. If the quantities d and the smaller diameter $D_1$ are uniform, then $D_2$ will be uniform if all elements of the coil are unwound to the limiting strain, $\epsilon_L$. The reduced diameter $D_1$ and enlarged diameter $D_2$ for a given stent are parameters which are dictated by the diameter of the vessel lumen where the prosthesis is to be deployed. For example, if the stent is to be enlarged from 0.125 inches to 0.25 inches and, assuming a limiting strain $\epsilon_L$=0.07, then $$0.07 = \frac{d}{0.125} - \frac{d}{0.25}$$

Solving this equation gives d=0.017 inches. This calculation demonstrates how one can select a wire diameter or strip thickness for the stent based on known dimensions of a vessel.

Figure 3:
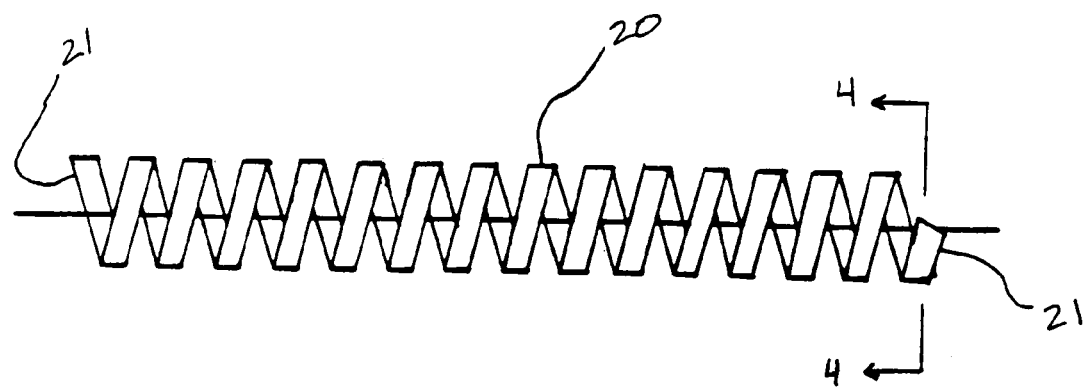
FIG. 3 depicts a helical prosthesis in accordance with the present invention.
Figure 4:
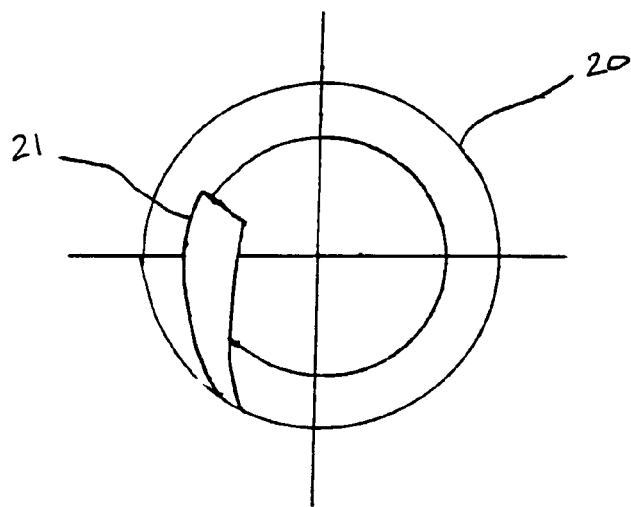
FIG. 4 is a cross-sectional view through section line 4-4 of the helical prosthesis depicted in FIG. 3.

FIG. 3 depicts an exemplary helical prosthesis for use in accordance with methods and apparatus disclosed herein. The helical prosthesis comprises a coiled wire or band 20 which terminates at ends 21. When viewed in cross-section, FIG. 4, it can be seen that the helical prosthesis or stent in one preferred embodiment has a periphery which is substantially circular, and therefore the outer surface of the stent defines a cylindrical volume. In other embodiments, the geometry of the stent may be varied to accommodate geometry of the body passageway where the stent will be deployed. For example, elliptical geometry may be used in certain passageways.

Figure 5:
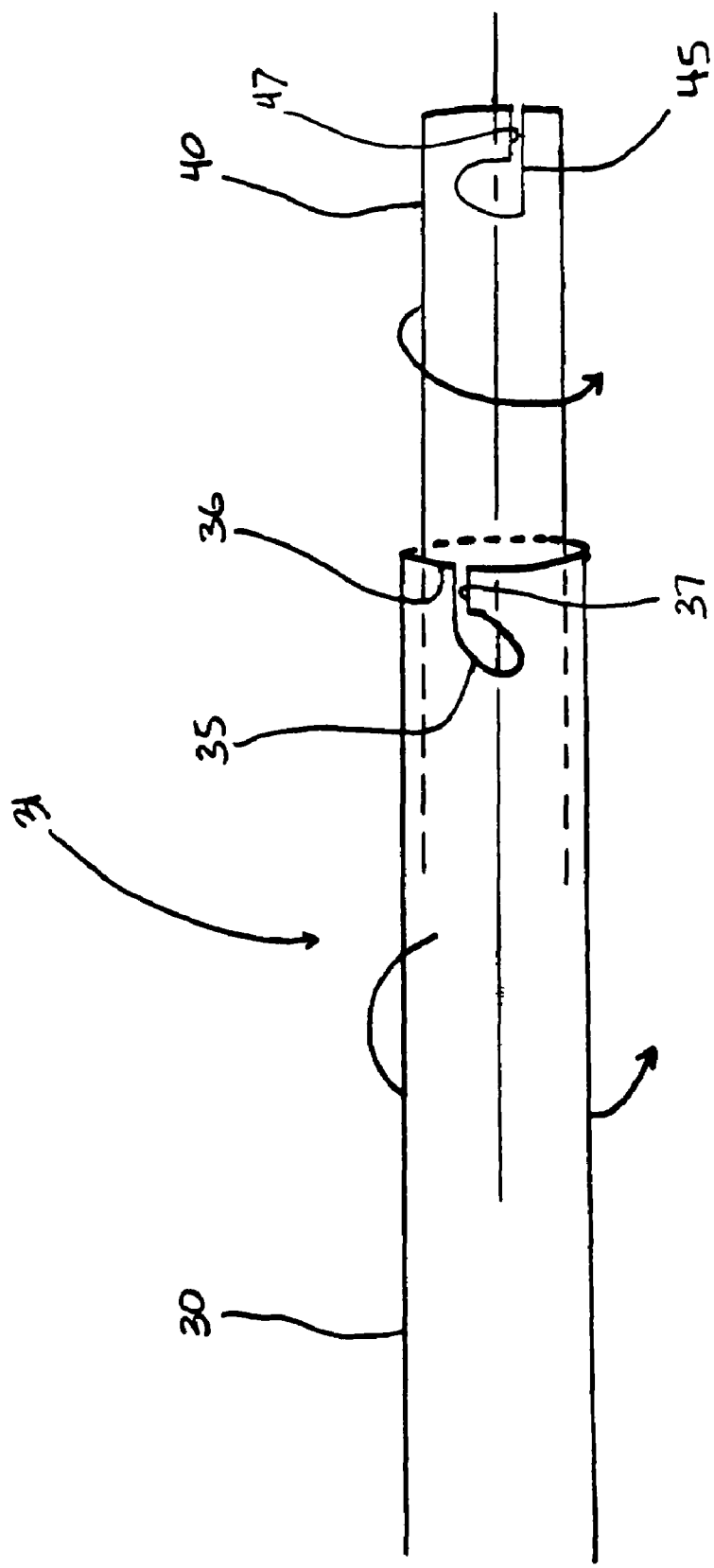
FIG. 5 depicts a preferred embodiment of a catheter according to the present invention.

FIG. 5 depicts one example of a preferred catheter for use in accordance with methods disclosed herein. The catheter has an elongate sheath 30, which comprises a proximal region (not shown) and a distal region 31 which terminates at distal opening 36. The sheath further includes a socket 35 which is shaped to receive and engage one of the ends 21 of stent 20. Slot 37 extends distally from socket 35 to distal opening 36 to provide a pathway to release the proximal end 21 of stent 20 after deployment of the stent. Extending from the distal opening 36 of sheath 30 is inner member 40 which, in one embodiment, is capable of both independent rotation and longitudinal translation relative to sheath 30. Inner member 40 also includes a socket 45 which is shaped to receive and engage the other end 21 of stent 20, and includes a slot 47 which provides a pathway between socket 45 and the distal end of inner member 40 to release the distal end 21 of stent 20 after deployment.

The catheter for use herein can be manufactured in accordance with methods disclosed in the art. The reader is referred to Limon, U.S. Pat. No. 5,476,505, for a description of one suitable design. The elongate sheath is produced from a material having good torque transmission properties, e.g., torque transmitting catheters as disclosed in Alston et al., U.S. Pat. No. 4,425,919. The inner member can be hollow or filled, and can be constructed in a design which resembles a speedometer cable, the construction and design of which are extensively described in the art. The inner member should have good torque transmission as well, and may alternatively include opposite helically wound cables as disclosed for a catheter drive shaft by Crowley et al., U.S. Pat. No. 4,951,677. In another embodiment, the sheath and inner member are constructed from two superelastic nitinol tubes which are coaxial. Moreover, the proximal end of the sheath and inner member (not shown in FIG. 5) may include a wheel with a handle attached to the sheath, and a crank attached to the inner member. These components permit transmission of torque to the sheath and inner member, and such components are produced in accordance with methods known in the art.

Figure 6:
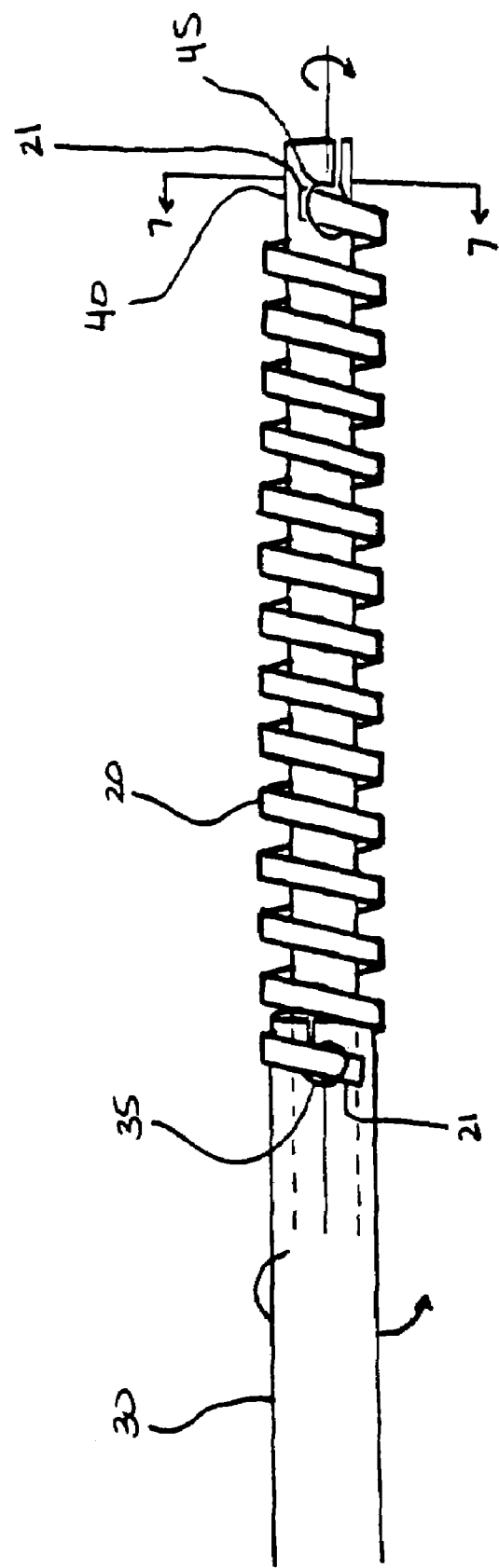
FIG. 6 depicts the catheter of FIG. 5 during unwinding of a helical prosthesis as shown in FIG. 3.
Figure 7:
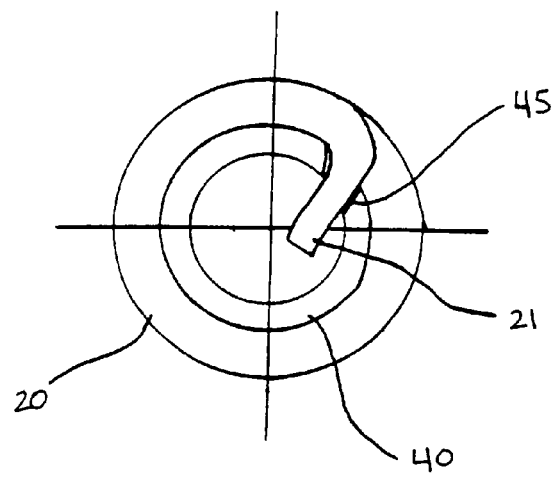
FIG. 7 is a cross-sectional view through section line 7-7 of the catheter and prosthesis depicted in FIG. 6.

FIG. 6 shows a preferred catheter having a stent loaded on its distal region and ready for deployment. Socket 35 receives and engages the proximal end 21 of stent 20, while socket 45 engages the distal end 21 of stent 20. FIG. 7 is a cross-sectional view of the distal region of inner member 40 through section line 7-7. As seen therein, stent end 21 of stent 20 passes through socket 45 of inner member 40 and is secured by the socket for unwinding.

The length of sheath 30 will generally be between 3 inches and 1 meter, with the diameter of the sheath generally 0.25-30 mm (0.01-1.2 inches), more preferably 0.5-25 mm (0.02-1 inch), more preferably 1-10 mm (0.04-0.4 inches), more preferably 2-5 mm (0.08-0.2 inches). The sockets 35 and 45 are slightly larger than the stent wire they engage. As explained above, the dimensions of the stent wire or strip depend on the strain, initial diameter, and final diameter desired for the stent. The plateau strain in the stent, $\epsilon_L$, depending on alloy, is a dimensionless quantity and will generally be in the range 1-8%, more preferably 2-8%, more preferably 3-8%, more preferably 4-8%, more preferably 5-8%. The length and diameter of the inner member will depend on the dimensions of the elongate sheath, and will be sized to permit sliding and rotational movement of the inner member coaxially within the sheath. The foregoing ranges are set forth solely for the purposes of illustrating typical device parameters. The actual dimensions of a device constructed according to the principles disclosed herein may obviously vary outside of the listed ranges without departing from those basic principles.

Figure 8:
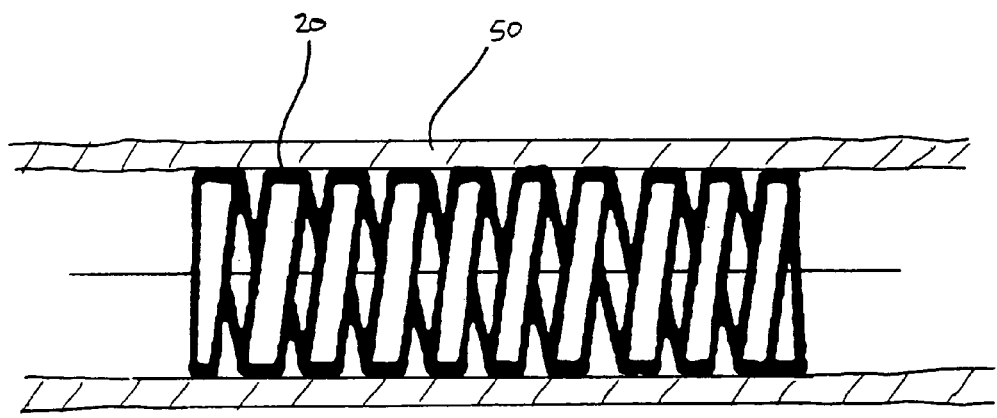
FIG. 8 depicts the helical prosthesis of FIG. 3 after placement in a vessel.

According to one embodiment, the catheter as depicted in FIG. 6 therefore has two coaxial elements 30 and 40 adapted to transmit torque to a pair of sockets 35 and 45, or other means for engaging opposite ends 21 of the coiled stent 20. Other examples of means for engaging the stent ends include snares, clips, clamps, grooves, and other suitable detachable/releasable means which are known equivalents to persons having skill in the art. Such examples, of course, are intended to be illustrative rather than limiting. The elements may be unwound relative to one another to, for example, place and enlarge a helical stent in a body lumen. The fact that the inner element passes inside the stent helps guide its expansion into final form. After placement, the catheter ends are disengaged from the stent ends 21 and removed to leave the enlarged stent in place as shown in FIG. 8.

In use, the catheter shown in FIG. 6 having a stent 20 disposed on the distal region will be advanced into a patient's body passageway until the distal region 31 of the elongate sheath 30 lies within a region of interest. The body passageway may be a blood vessel, and the region of interest may be an area narrowed by a stenotic lesion. In one embodiment, a guidewire is used to assist the advancement of the catheter into the body passageway. Fluoroscopic imaging can be used to determine proper positioning of the catheter, and for this reason the sheath or the inner member 40 may include one or more radiopaque markers to assist with positioning. Once the stent is in place, the sheath 30 and inner member 40 are operated to transmit torque to opposite ends 21 of stent 20. As will be apparent to those skilled in the art, both the sheath and inner member may be rotated, or the sheath may be held stationary while the inner member is rotated, or alternatively, the inner member may be held stationary while the sheath is rotated. Any of these alternatives will permit unwinding of the spring-like stent to effect its enlargement in the body passageway. According to the embodiment depicted in FIG. 6 as viewed in cross-section from the distal end (FIG. 7), sheath 30 is rotated clockwise relative to inner member 40 to produce an enlargement of stent 20. Either sheath 30 or inner member 40 may be held stationary. When desired, the wire element of stent 20 may have a uniform diameter and the helix at any cross-section is of uniform diameter. If these conditions are met, then unwinding of the helical prosthesis at the limiting strain produces an enlarged helical prosthesis of uniform and predictable expanded diameter. Alternatively, this shape may be arbitrarily non-uniform. After unwinding, the stent is released from sockets 35 and 45 by withdrawing inner member 40 and sheath 30 so that distal and proximal stent ends 21 slide through slots 37 and 47, respectively. The enlarged stent is then left in the vessel as depicted in FIG. 8.

The catheter described herein can also be used to retrieve and remove an implanted helical prosthesis from a body passageway. A catheter as depicted in FIG. 5 is positioned within a body passageway so that the sheath 30 and inner member 40 lie in close proximity to proximal and distal ends 21, respectively, of stent 20. Socket 35 is then used to engage the proximal end 21 of stent 20 by sliding stent end 21 through slot 37, while socket 45 is used to grab or engage the distal end of stent 20 in a similar manner using slot 47. Once both ends 21 of stent 20 are engaged, the sheath and inner member can be rotationally operated to wind the helical prosthesis to reduce the helical prosthesis to a smaller diameter. Once the diameter is reduced, the stent and catheter can be removed from the body passageway or vessel.

Figure 9:
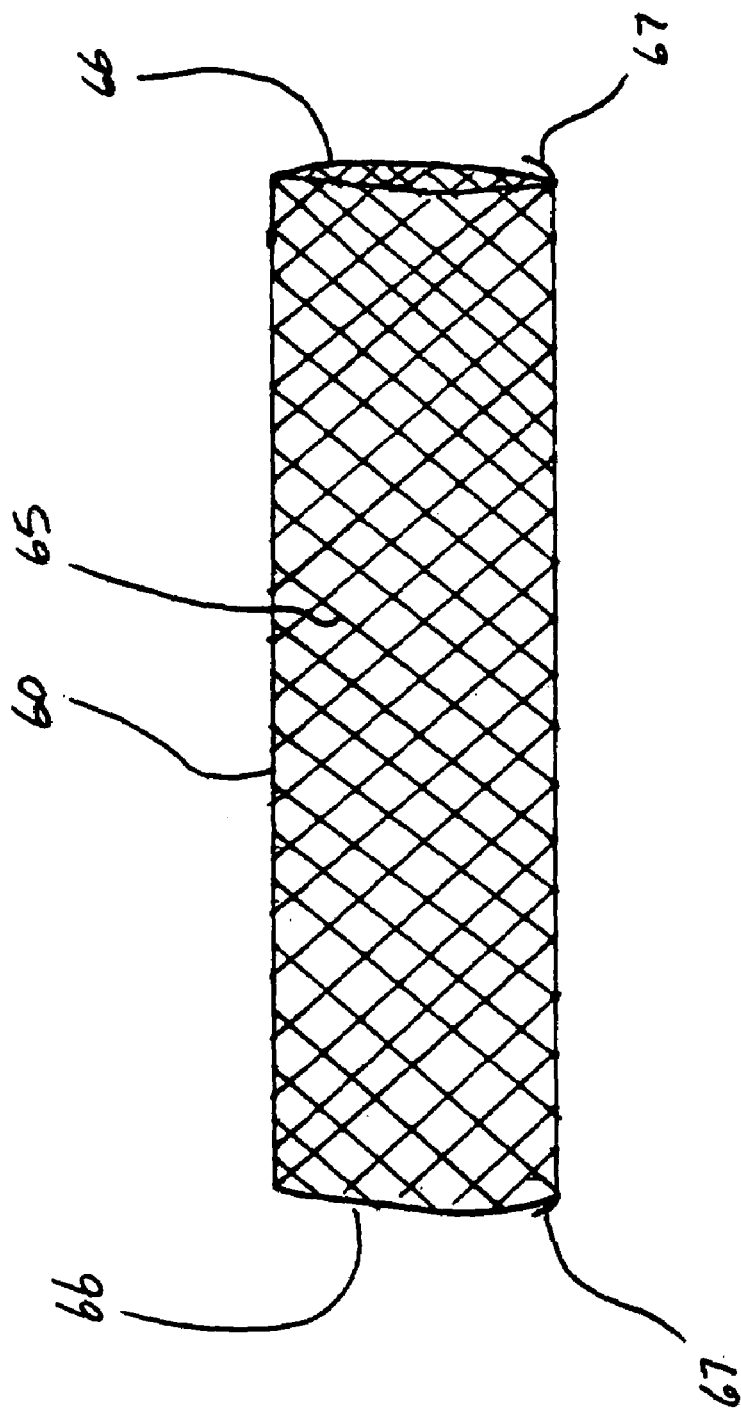
FIG. 9 depicts a stent in accordance with an alternative embodiment of the present invention.
Figure 10:
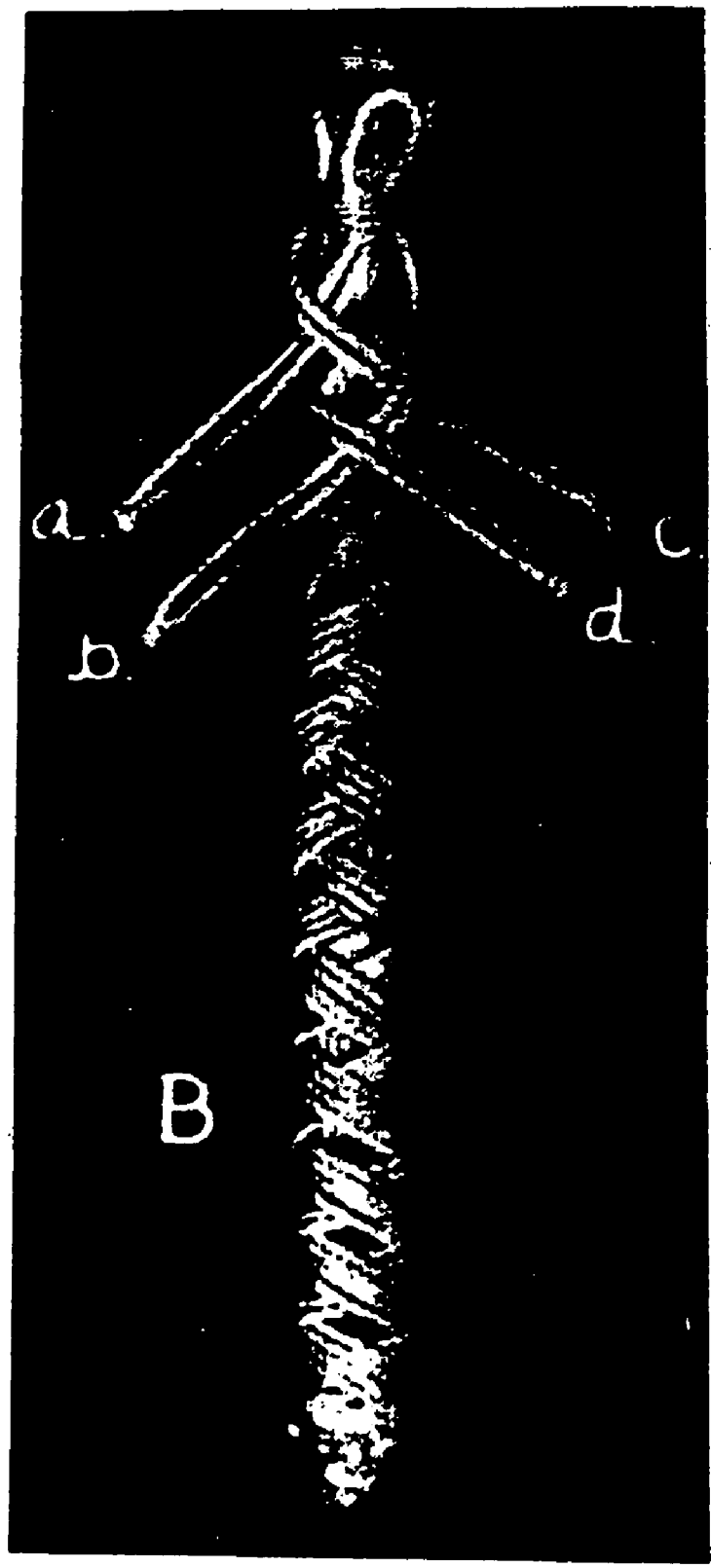
FIG. 10 depicts a braided structure suitable for application to an interwoven stent in accordance with an alternative embodiment of the present invention.

In accordance with another embodiment, FIG. 9 depicts an alternative prosthesis which is also capable of radial enlargement by application of mechanical force. In this embodiment, the stent 60 comprises an interwoven mesh of wires 65 in a design that resembles a braid (including a so-called Turks Head, or a stent with mutually interlocking filaments as disclosed by Amstrup, U.S. Pat. No. 5,476,508), or an expanded metal cage. FIG. 10 depicts a braid construction which is suitable for use herein, and it will be understood by those skilled in the art that alternative braids can also be used, such as the more common version comprising a weave characterized as over two-under two. FIGS. 11, 11A, 12, and 12A depict examples of a Turk's Head, where the effect is similar to a braid, but the construction is from one strand, sometimes doubled after the first pass. Alternative designs for stents comprising interwoven meshes can be produced from materials described herein in accordance with woven structures disclosed in Graumont et al., Encyclopedia of Knots and Fancy Rope Works, Cornell Maritime Press (1945), and further discussion of braids and Turk's Heads can also be found therein.

Deployment of this stent does not rely on torsional unwinding, but instead requires longitudinal compression, wherein the proximal and distal ends 66 of the stent are moved closer together. Accordingly, the stent includes end features 67 which are engaged by means for grabbing which are associated with the catheter. Once the end features are engaged, the grabbing means are operated to longitudinally compress the stent ends and thereby radially expand the stent.

In another embodiment, the stent takes the form of a spirally-wrapped sheet, as previously discussed by Kreamer, U.S. Pat. No. Re. 34,327, and Garza et al., U.S. Pat. No. 4,665,918. Laid flat, the sheet would have a substantially rectangular, or preferably a substantially trapezoidal shape. The sheet is rolled into a spiral, which shape is suitable for deployment. As rolled, the innermost edge extends proximally and distally beyond the outermost edge, and thus both the inner and outer edges are thereby available to be engaged by means for grabbing. The grabbing means can then be counter-rotated to cause radial expansion.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A catheter system for enlargement of a body passageway, said catheter system comprising:
   a prosthesis having proximal and distal ends and comprising a material having plateau behavior and incomplete hysteresis on unloading;
   an elongate assembly having proximal and distal regions, said distal region adapted to enter the body passageway while said proximal region extends outside of the body passageway to permit control of said catheter, said assembly comprising:
   a first member having a prosthesis socket defined in an outer wall thereof and adapted to receive and engage said proximal end of said prosthesis;
   a second member having a prosthesis socket defined in an outer wall thereof and adapted to receive and engage said distal end of said prosthesis, wherein said first member and said second member are adapted for relative movement and wherein at least one of said first and second members includes a slot defined in and originating in the outer wall and extending to the prosthesis socket thereof.

2. The catheter system of claim 1, wherein the prosthesis defines a substantially helical shape.

3. The catheter system of claim 2, wherein said first member and said second member each comprise a pair of coaxial elements, said coaxial elements adapted to transmit torque to opposite ends of said helical prosthesis.

4. The catheter system of claim 3, wherein said helical prosthesis includes one or more elongate strands, each having proximal and distal ends.

5. The catheter system of claim 4, wherein said material has martensitic properties ranging from about 30 degrees to about 42 degrees Celsius.

6. The catheter system of claim 5, wherein said helical prosthesis exhibits a plateau limit strain of 2-8%.

7. The catheter system of claim 4, wherein said helical prosthesis exhibits pseudoelastic properties.

8. The catheter system of claim 6, wherein said material comprises an alloy of Ni, Ti, and V.

9. The catheter system of claim 8, wherein the atomic percent-composition of Ni:Ti:V is selected from the group consisting of 41.5:38.5:20.0, 36.25: 33.75:30.0, 47.75:45.75: 6.5, 47.5:45.5:7.0, 48.5:46.5:5.0, 45.0:45.0:10.0, 47.5:46.5: 6.0, 46.5:46.5:7.0, 48.25:46.25:5.5, and 48.0:46.0:6.0.

10. A system for supporting a body vessel, which comprises:
   a catheter adapted for introduction and manipulation within a body vessel, the catheter including an outer member defining a longitudinal axis and an inner member disposed within the outer member, the inner member and the outer member adapted for relative rotational and longitudinal movement with respect to the longitudinal axis, at least one of the inner member and the outer member including a slot defined in an outer wall portion and extending to a prosthesis socket; and
   a prosthesis adapted for positioning within a body vessel to support an interior wall of the body vessel, the prosthesis having a trailing end releasably mounted to the outer member of the catheter and a leading end releasably mounted to the inner member of the catheter, at least one of the trailing end and the leading end being received within the prosthesis socket of the at least one of the inner member and the outer member, the prosthesis adapted to assume a reduced state having a reduced transverse dimension upon relative rotational movement of the inner and the outer members, to thereby facilitate passage of the prosthesis within the body vessel.

11. The system according to claim 10 wherein each of the inner member and the outer member includes a slot defined in an outer wall portion and extending to a prosthesis socket.

12. The system according to claim 10 wherein the prosthesis socket is radially offset from the slot.

13. The system according to claim 10 wherein the prosthesis comprises a material selected from the group consisting of Ni, Ti and V.

14. The system according to claim 10 wherein the prosthesis comprises a shape memory material.

15. The system according to claim 10 wherein the prosthesis defines a substantially helical coiled configuration.

16. The system according to claim 10 wherein the inner member and the outer member are adapted for relative longitudinal movement to define a reduced transverse dimension of the prosthesis, to thereby facilitate passage of the prosthesis within the body vessel.

17. A system for supporting a body vessel, which comprises:
   a catheter adapted for introduction and manipulation within a body vessel, the catheter including an outer member defining a longitudinal axis and an inner member disposed within the outer member, the inner member and the outer member adapted for relative rotational and relative longitudinal movement with respect to the longitudinal axis, at least one of the inner member and the outer member includes a prosthesis socket defined in a wall portion thereof for receiving a respective trailing and leading end of a prosthesis, the one of the inner member and the outer member further includes a slot defined in and originating in the wall portion and extending to the prosthesis socket for facilitating mounting of the respective trailing and leading end within the prosthesis socket; and
   the prosthesis adapted for positioning within a body vessel to support an interior wall of the body vessel, the prosthesis having a trailing end releasably mounted to the outer member of the catheter and a leading end releasably mounted to the inner member of the catheter, the prosthesis adapted to assume a reduced state having reduced transverse dimension upon relative longitudinal movement of the inner and the outer members, thereby facilitating passage of the prosthesis within the body vessel.

18. The system according to claim 17 wherein the prosthesis comprises a material selected from the group consisting of Ni, Ti and V.

19. The system according to claim 17 wherein the prosthesis comprises a shape memory material.

20. The system according to claim 17 wherein the prosthesis defines a substantially helical coiled configuration.

21. The system according to claim 17 wherein the prosthesis socket is radially offset from the slot in the wall portion.

22. The system according to claim 17 wherein each of the inner member and the outer member includes a prosthesis socket within a respective wall portion of the inner and the outer member.

23. The system according to claim 22 wherein each of the inner member and the outer member includes a slot defined in the respective wall portion thereof.

* * * * *